United States Patent [19]

Abiru et al.

[11] Patent Number: 4,768,951
[45] Date of Patent: Sep. 6, 1988

[54] DENTAL TRAY

[75] Inventors: Masao Abiru, Omiya; Bunsaku Yoshida, Ichikawa; Shiro Kono, Kokubunji, all of Japan

[73] Assignee: G-C Dental Industrial Corp., Tokyo, Japan

[21] Appl. No.: 74,027

[22] Filed: Jul. 16, 1987

[30] Foreign Application Priority Data

Aug. 13, 1986 [JP] Japan .................................. 61-188673

[51] Int. Cl.⁴ .................................................. A61C 9/00
[52] U.S. Cl. .......................................... 433/48; 433/37
[58] Field of Search ..................................... 433/37, 48

[56] References Cited

U.S. PATENT DOCUMENTS 4,161,065  7/1979  Gigante .................................. 433/37
4,553,936  11/1985  Wang ..................................... 433/37

Primary Examiner—Robert Peshock
Attorney, Agent, or Firm—Oblon, Fisher, Spivak, McClelland & Maier

[57] ABSTRACT

A dental tray of a shape suitable for direct contact with the mucosal surface of the mouth and capable of retaining an impression making material thereon comprising a thermoplastic resin material transparent to activating light energy radiation and which is softenable at a temperature ranging from 40°–70° C.

5 Claims, 1 Drawing Sheet

DENTAL TRAY

BACKGROUND OF THE INVENTION

1. Field of the Invention

The present invention relates to a dental tray. More particularly, the present invention is concerned with a dental tray designed to be used for preparing the denture bases of plate dentures, precise impression-taking with the use of light-curing materials and curing the light-curing materials filled in teeth cavities.

2. Statement of the Prior Art

In the present disclosure, the term "denture base" refers to a plate portion forming the base of a plate denture and coming into direct contact with the mucosal surface of the cavity. Thus, the denture base is a part of the plate denture serving to stably maintain the plate denture in the oral mouth and transmit the occlusal pressure to the mucosal surface of the oral cavity, and is the core of the finished plate denture. In general, the denture bases of plate dentures are prepared through very numerous steps by an indirect method with heat- or light-curing resins.

The preparation of the denture bases with a heat-curing resin involves the so-called "preparatory steps" for reproducing the intramouth state on a working model, which comprises:

taking a preliminary impression using a ready-made tray and an impression material, pouring gypsum slurry into the obtained preliminary impression to form a gypsum model, pressing a self curing resin against the gypsum model to form an individual tray, taking a precise impression using the individual tray obtained and an impression material, and pouring gypsum slurry into the obtained precise impression to form a working model. After the preparatory steps, the denture bases are prepared by the steps of:

forming a bite plate on the working model with wax and attaching it to an articulator, arranging artificial teeth on the bite plate to form a wax denture, placing the wax denture in a dental flask and investing it in gypsum, filling a heat-curing resin in the vacant space of the wax denture removed and curing, and digging up the cured resin, followed by polishing.

Thus, the denture bases and plate dentures are prepared through very numerous steps. As disclosed in Japanese Patent Laid-Open Publication No. 60(1985)-90552, on the other hand, the preparation of denture bases and plate dentures using a light-curing resin involves the so-called "preparatory steps" for reproducing the intramouth state on a working model, which comprise:

taking a preliminary impression using a ready-made tray and an impression material, pouring gypsum slurry into the obtained preliminary impression to form a gypsum model, pressing a self curing resin against the gypsum model to form an individual tray, taking a precise impression using the individual tray obtained and an impression material, and pouring gypsum slurry into the obtained precise impression to form a working model. After the preparatory steps, the denture bases are prepared by the steps of pressing a light-curing resin against the working model and applying active energy rays to the resin for the polymerization and curing thereof. To finish the plate dentures, formation of alveolar ridges portion, arrangement of artificial teeth and formation of gingival portion are further formed on the obtained denture bases with the use of a light-curing resin.

In the case of the denture bases of plate dentures obtained through such steps, it is impossible to remove errors occurring in the course of the preparatory steps of preparing the denture bases wherein the intramouth state is reproduced on the working model, since they are prepared on the basis of the working model. Nor is their fitting accuracy satisfactory. Further, very numerous steps are still required to prepare the denture bases of plate dentures.

That the steps of preparing the denture bases of plate denture is very numerous and difficulty is encountered in obtaining the denture bases of improved fitting accuracy is considered to be attributable to the fact that the dental tray is designed only for the purpose of taking impressions in the course of the so-called "preparatory steps" wherein the intramouth state is reproduced on the working model, and to the prejudice that the dental tray should not, or cannot, be used for the main steps of the preparation of denture bases.

The prior art dental trays include a ready-made tray for preliminary impression-taking and an individual impression tray for precise impression-taking and individual tooth impression tray for each tooth impression-taking. These trays have been provided for the exclusive purpose of taking impressions in the steps wherein the intramouth state is reproduced on the working model. Thus, the ready-made and individual trays have generally been made of a metallic or hard plastic material and a self curing resin or organic compound, respectively, with a main view to preventing them from transforming easily due to the forces applyed thereto during the pressing step or removal step of impressions. In other words, any substantial attention has not been paid to their active energy rays-transmitting property. Nor has any consideration been taken into account as regards the possibility that they might have been used for the later steps in preparing the denture bases of plate dentures. As the dental trays having active energy rays-transmitting property, Japanese Patent Laid-Open Publication No. 61(1986)-41447 discloses a dental tray comprising a transparent rigid material such as transparent hard plastics or glass. However, the dental tray disclosed in this Japanese Patent Laid-Open Publication No. 61(1986)-41447 is a ready-made tray designed to be exclusively used for impression-taking in the course of the steps of reproducing the intramouth state on the working model, as is the case with the conventional dental tray. For that reason, certain limitation is previously imposed upon the size and shape of such a dental tray by the manufacturer, and is formed of a rigid material difficult to transform, so that it cannot be transform to suit the intramouth contour, and thus be used as an individual tray. Thus, although it is possible to use the dental tray disclosed in Japanese Patent Laid-Open Publication No. 61(1986)-41447 as a ready-made tray for preliminary impression-taking, yet it is difficult to use such a dental tray as the individual tray for precise impression-taking. Still more, it is very difficult to use such a dental tray for the preparation of the denture bases of plate denture.

SUMMARY OF THE INVENTION

A main object of the present invention is to destroy the conventional conservative idea and develop a dental tray suitable for the preparation of the denture bases of plate dentures. In accordance with the present invention, it has been found that such a dental tray should possess all the following properties.

It is easily transformable according to the intramouth state of an individual to provide an individual tray.

It is not easily transformed due to the forces applied thereto during the pressing or removal step in the course of impression taking.

It transmits active energy rays capable of curing a light-curing resin placed on its inside face simultaneously with precise impression-taking.

It allows easy separation of the cured resin therefrom without any transformation of said resin. And, It is capable of being sterilized with chemicals for repeated use.

The present invention provides a dental tray which possesses all the aforesaid properties. As a result, the present invention renders it possible to prepare the denture bases of plate dentures through a much smaller number of steps, i.e., through the steps of forming an individual tray; placing a light-curing resin on the inside face of the tray to take a precise impression of the intramouth state and polymerizing and curing the resin as such; and separating the cured resin from the tray, whereby the cured resin itself gives a denture base, and thus making itself an epoch-making invention. The denture bases of plate dentures according to the present invention are incomparably superior in the fitting accuracy to those obtained through the conventional steps.

Even in the case of precise impression-taking, the individual tray therefor can easily be prepared within a short time in a direct manner, and dispenses with the steps of taking a preliminary impression with the use of a ready-made tray and an impression material, pouring gypsum slurry into the obtained preliminary impression to form a gypsum model and pressing a self curing resin against the gypsum model to form an individual tray, as conventionally required. The obtained individual tray enables a light-curing impression material to be used for precise impression-taking.

As a result of extensive studies made of a dental tray satisfying all the properties required therefor, the present inventors have found that a material capable of transmitting active energy rays and being thermally softened is effective for such a dental tray.

In other words, the dental tray according to the present invention comprises a material capable of tranmitting active energy rays and being thermally softened. In order to prepare the denture base of a plate denture, the dental tray according to the present invention is first warmed and softened in warm water, etc., whereby it is transformed according to the intramouth state, making use of its heat softening property, and is cooled and hardened as such in cold water, etc. to form an individual tray. Then, a light-curing resin is placed on the inside face of the tray for functional impression manipulations, while active energy rays are directly introduced into the tray from the outside face thereof, whereby the light-curing resin placed on the inside face of the tray is uniformly cured within a short time, making use of its active energy rays-transmitting properties. Thereafter, the tray is again warmed and softened in warm water, etc., making use of its heat softening property, and the light-cured resin is separated from the tray. This light-cured and separated resin directly provides the denture base of a plate denture.

DETAILED DESCRIPTION OF THE INVENTION

In general, thermoplastic resins may be used as the materials capable of transmitting active energy rays and being thermally softened. Among such thermoplastic resins, however, those suitable as the materials having both active energy rays-transmitting property and heat softening property and the usable for the dental trays of the present invention are the type of thermoplastic resin which is transparent and has a softening point of 40° to 70° C. More specifically, this type of thermoplastic resin has the active energy rays-transmitting properties of transmitting active energy rays introduced from the outside face of the dental tray to a light-curing resin placed on the inside face thereof and sufficiently polymerizing and curing the resin, shows a strength such that it is not easily transformed due to the forces applied thereto during the pressing or removal step in the course of impression-taking, and possesses the heat softening property of being easily transformable according to the intramouth state by hand pressure and softened to such an extent that the dental tray is easily transformable and separated from the light-curing resin polymerized and cured. With a resin of no transparency, it is impossible to obtain sufficient active energy rays-transmitting, property. On the other hand, a resin having a softening point of below 40° C. tends to be easily transformed at a temperature (about 37° C.) prevailing in the oral cavity, while a resin having a softening point exceeding 70° C. is hard to transform.

Any material having both active energy rays-transmitting property and heat softening property may be used for the dental trays of the present invention. The styrene based plastics used may include polystyrene and its derivatives; the acrylate based plastics, polyacrylate and its derivatives as well as polymethacrylate and its derivatives; the fluorine based plastics, polytetrafluoroethylene and its derivatives, polyvinyl fluoride and its derivatives and polychlorotrifluorethylene and its derivatives; the diene based plastics, polybutadiene and its derivatives and polyisoprene and its derivatives; the urethane based plastics, polyurethane and its derivatives; and the ethylenical based plastics, ethylene copolymers and their ionomer resins.

Due to their high active energy rays-transmitting property and softening point of 40° to 70° C., the ionomer resins of ethylene copolymers are, among them, particularly preferred.

More specifically, the ionomer resins of ethylene copolymers may be obtained by the reaction of the base copolymers with metal ions capable of ionizing them.

The base copolymers used may include ethylene/acrylic acid copolymers, ethylene/methacrylic acid copolymers, ethylene/itaconic acid copolymers, ethylene/hydrogen methyl maleate copolymers, ethylene/maleic acid copolymers, ethylene/acrylic acid/methyl methacrylate copolymers, ethylene/methacrylic acid/ethyl acrylate copolymers, ethylene/itaconic acid/methyl methacrylate copolymers, ethylene methyl maleate/ethyl acrylate copolymers, ethylene/methacrylic acid/vinyl acetate copolymers, ethylene/acrylic acid/vinyl alcohol copolymers, ethylene/propylene/acrylic acid copolymers, ethylene/styrene/acrylic acid copolymers, ethylene/methacrylic acid/acrylonitrile copolymers, ethylene/fumaric acid/vinyl methyl ether copolymers, ethylene/vinyl chloride/acrylic acid copolymers, ethylene/vinylidene chloride/acrylic acid copolymers, ethylene/vinyl fluoride/methacrylic acid copolymers, ethylene/chlorotrifluoroethylene/methacrylic acid copolymers and the like.

The metal ions to react with and ionize such base copolymers include $Na^+$, $K^+$, $Li^+$, $CS^+$, $Ag^+$, $Cu^+$, $Mg^{2+}$, $Ca^{2+}$, $Sr^{2+}$, $Ba^{2+}$, $Cu^{2+}$, $Sn^{2+}$, $Fe^{2+}$, $Ni^{2+}$, $Zn^{2+}$, $Al^{3+}$, $Sc^{3+}$, $Fe^{3+}$, $Yt^{3+}$ and the like.

In order to enhance the physical properties of the dental trays, fillers may be added to these materials. The amount of such fillers to be added should preferably be less than 70 weight % based on the total weight of the present dental trays. With the fillers being used in an amount of higher than 70 weight %, the active energy rays-transmitting property drop, while no sufficient heat softening property is obtained.

Usable as the fillers are calcium carbonate, molten powdery calcium, titanium dioxide, zirconium silicate, aluminium silicate, silica, M. M. A. polymers, vinyl chloride powders, alumina, glass, kaolin, anhydrous silicic acid, hydrous silicic and the like. Among them, preference is given to M. M. A. polymers, glass, and anhydrous.hydrous silicic acid, each of high transparency, with the transmittance of active energy rays in mind. If required, it may further be possible to take some means, e.g., to embed a metallic wire in the dental tray so as to enhance the strength thereof. It is understood that the dental trays of the present invention may be colored to such an extent that their active energy rays-transmitting property is not inhibited.

It is also preferred that the materials having both active energy rays-transmitting property and heat softening property according to the present invention excel in the resistance to attack by chemicals such as alcohols, carbolic acid, chlorohexyzine and cationic soap etc., since they should be sterilized and cleaned by immersion in aqueous solutions thereof for repeated use.

For further convenience, the so-called "temperature indicator" which changes in color tone with temperature is previously contained in the materials having both active energy rays-transmitting property and heat softening property, since the softened state of the dental trays by heat can then be ascertained through changes in color tone.

If required, it may be possible to take appropriate means through which the active energy rays introduced from the outside face of the dental tray is guided to the inside face thereof, e.g., optical fiber means previously embedded in the dental tray.

The dental trays of the present invention may take the form of a edentulous or dentulous tray for the full jaws and a unilateral or partial tray for the unilateral jaw, and are thus similar in the shape to the conventional dental trays. However, the dental trays of the present invention are not limited to such shapes, and may optionally be in the form of a flat shape. For the purpose of improving the retaining force with which the light-curing material such as a light-curing resin is retained on the inside face of the dental tray according to the present invention, it may be provided with an appropriate retaining mechanism defined by provided surface roughness, for instance.

Any particular inlet means for the introduction of active energy rays are not necessarily provided with the dental tray of the present invention, as long as the active energy rays introduced from any position of the outside face of the tray pass therethrough, and cured the light-curing material placed on the inside face thereof. If required, however, such an inlet may be formed in the outside face of the tray. It may also be possible to cover or bond the portion of the outside face of the tray, except for the inlet, with a metal or a resin which is the same as that forming the tray, and is filled with a metal filler so as to provide a mirror surface, whereby the diffusion or reflection of active energy rays can be prevented.

The term "active energy rays" used in this disclosure refers to visible or ultraviolet rays.

BRIEF DESCRIPTION OF THE DRAWINGS

The trays of the present invention will now specifically be explained with reference to the accompanying drawings, in which.

Figure 1:
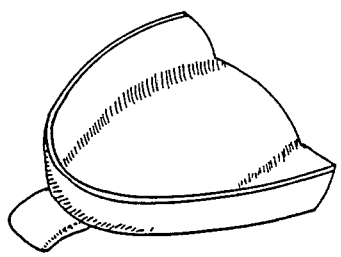
FIG. 1 is a perspective view of the dental tray for the full upper jaw according to the present invention.
Figure 2:
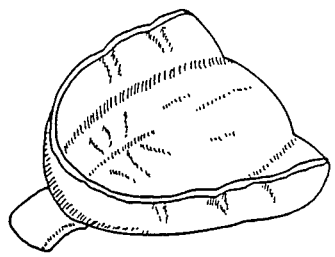
FIG. 2 is a perspective view of the individual tray after the dental tray of FIG. 1 has been transformed according to the intramouth contour.
Figure 3:
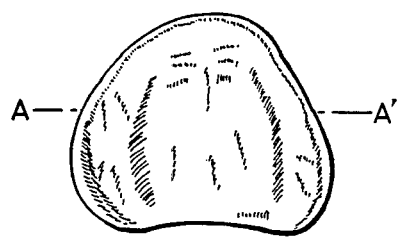
FIG. 3 is a view of the denture base of a plate denture, as viewed from the mucosal side, said denture base being formed of a light-curing resin using the individual tray of FIG. 2.

The dental tray for the full upper jaw, shown in FIG. 1, is molded into a substantially semi-elliptical shape previously provided with a U-shaped groove by injecting into a mold an ionomer resin obtained by the reaction of an ethylene/methacrylic acid copolymer with $Na^+$, which is used as the material having the active energy rays-transmitting property and the heat softening property. This dental tray is transparent, has a strength such that it is not easily transformed at room temperature by the forces applied thereto during the pressing or removal step in the course of impression-taking manipulations, and possesses the property of being softened to such a degree that it is easily transformable by hand pressure, when warmed. Referring to the preparation of the denture base of a plate denture (full denture) with the dental tray, the dental tray illustrated in FIG. 1 is first immersed in warm water where it is warmed and softened. Then, it is put over an application surface on which a spacer is placed, and is transformed according to the intramouth contour. Cold water is applied on the dental tray in this state for cooling and hardening, whereby a tray, illustrated in FIG. 2, is formed. A light-curing resin is placed on the inside face of the obtained tray for functional impression manipulations. In this state, active energy rays are introduced from an arbitrary position on the outside of the tray to polymerize and cure the resin on the inside face of the tray. Subsequently, the cured resin is immersed in warm water together with the tray to warm and soften only the tray portion and separate it from the cured resin. In this manner, the denture base of a plate denture having improved fitting accuracy, as illustrated in FIG. 3, is defined by the thus separated cured resin.

Destroying the conventional idea that the dental tray can or should be used only for the purpose of impression-taking in the step of reproducing the intramouth state on a working model, the dental tray of the present invention makes itself epoch-making in dentistry in that it can be used direct for the preparation of the denture base of a plate denture.

It is understood that the dental tray of the present invention is applicable not only to the preparation of the denture base of a plate denture as mentioned above, but also to the precise impression-taking required for the preparation of prostheses appliance such as crowns, bridges or metal dentures, since it m,akes it easy to directly form an individual tray which allows precise impression-taking with a light-curing impression material. More specifically, the dental tray of the present invention dispenses with the preparation of an individual tray which involves a succession of troublesome steps of obtaining a preliminary impression with a ready-made tray and an impression material, pouring gypsum slurry into the preliminary impression and pressing a self curing resin against the gypsum model for setting, as conventionally carried out during precise impression-taking. In other words, the dental tray of the present invention renders it possible to obtain an individual tray in a very simple manner wherein it is warmed and softened, then transformed according to the intramouth state, and finally cooled and hardened, and allows precise impression-taking using a light-curing impression material which has not invited any attention at all, when using the conventional individual tray.

It is understood that the present dental tray is suitable for use not only with a light-curing material, but also with the conventional impression-taking materials cured by chemical reactions such as alginate or rubber based ones. Further, the dental tray of the present invention may effectively be used to cure a dental light-curing filling material filled in teeth cavities, such as a light-curing composite resin or cement.

EXAMPLES

The present invention will now be explained in greater detail with reference to the examples.

EXAMPLE 1

The preparation of the dental tray for the full upper jaw and the denture base of a plate denture (full denture) was in the following manner.

(1) Using an ionomer resin (manufactured by Mitsui.Du Pont Polychemical Co., Ltd. and sold under the trade name of HI.MILAN) obtained by the reaction of an ethylene/methacrylic acid copolymer with $Na^+$ as the thermoplastic resin which was transparent and softened by warming to about 60° C., a dental tray for the full upper jaw having the shape as illustrated in FIG. 1 was prepared by injection molding in a mold.

(2) A spacer of a given thickness to define the thickness of the denture base in the later stage was placed on the edentulous region of the full upper jaw. Thereafter, the dental tray previously softened in warm water of 65° C. was put on the spacer. Cold water was then applied on the tray to cool and harden it, while it was transformed according to the intramouth shape. Subsequently, the spacer was removed from the dental tray to prepare an individual tray (FIG. 2).

(3) A light-curing resin was placed on the inside face of the obtained individual tray for functional impression manipulations such as muscle trimming. In this state, the supply inlet in a commercially available active energy rays radiation unit (manufactured by ICI Co., Ltd. and sold under the trade name of LUXOR) was brought into contact with an arbitrary position of the outside face of the tray for 3-minute visible rays irradiation, whereby the resin was polymerized and cured.

Figure 4:
FIG. 4 is an end view of the denture base taken along the line A—A' of FIG. 3.

(4) The cured resin was immersed together with the tray in warm water of 65° C., whereby the tray portion alone was softened. The cured resin was then separated from the tray, thus giving the denture base of the plate denture having satisfactory fitting accuracy (FIGS. 3 and 4).

EXAMPLE 2

The partial tray and the denture base of a plate denture (partial denture) were prepared in the following manner.

Figure 5:
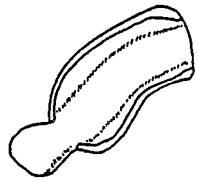
FIG. 5 is a perspective view of the partial tray according to the present invention.

(1) Using a plate-like ionomer resin (manufactured by Mitsui.Du Pont Polychemical Co., Ltd. and sold under the trade name of HI.MILAN) obtained by the reaction of an ethylene/methacrylic acid copolymer with $Zn^{2+}$ as the thermoplastic resin which was transparent and softened by warming to about 50° C., a partial tray having the shape as illustrated in FIG. 5 was prepared by stamping in a warmed state.

Figure 6:
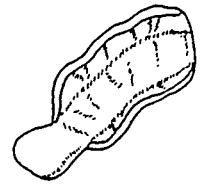
FIG. 6 is a perspective view of the individual tray after the dental tray of FIG. 5 has been transformed according to the intramouth contour.

(2) At a missing teeth portion in the left lower molar region was placed a spacer of a given thickness to define the thickness of the denture base of a plate denture at the later stage. The remaining teeth were blocked out for the try-in of a separately prepared clasp of a metal. Thereafter, the dental tray previously softened in warm water of about 60° C. was placed over the spacer. While it was transformed according to the intramouth shape, cold water was applied thereto for cooling and hardening. Then, the spacer was removed from the dental tray to prepare an individual tray (FIG. 6).

(3) A light-curing resin was placed on the inside face of the obtained individual tray for functional impression manipulations such as muscle trimming. In this state, the supply inlet in a commercially available active energy rays radiation unit (manufactured by ICI Co., Ltd. and sold under the trade name of LUXOR) was brought into contact with an arbitrary position of the outside face of the tray for 2-minute visible rays irradiation, whereby the resin was polymerized and cured.

(4) The thus cured resin, the metallic clasp and the tray were immersed together in warm water of 60° C. to soften and separate only the tray, thus leaving the denture base of a plate denture having satisfactory fitting accuracy, wherein the metallic clasp was ideally retained by the cured resin.

EXAMPLE 3

The preparation of a dental tray for the full upper jaw and the precise impression-taking with a light-curing impression material were carried out in the following manner.

(1) Using an ionomer resin obtained (manufactured by Mitsui.Du Pont Polychemical Co., Ltd. and sold under the trade name of HI.MILAN) by the reaction of a ethylene/methacrylic acid copolymer with $Na^+$ as the thermoplastic resin which was transparent and softened by warming to about 55° C., a dental tray for the full upper jaw having the shape as illustrated in FIG. 1 was prepared by injection molding in a mold.

(2) The dental tray previously softened in warm water of 60° C. was placed over a spacer placed on an application surface the impression of which was to be taken. While the tray was transformed according to the contour of that application surface, cold water was applied to the tray for cooling and hardening. Subsequent removal of the spacer gave an individual tray.

(3) A light-curing impression material was placed on the inside face of the obtained individual tray, and was pressed against said application surface. At an arbitrary position on the outside face of the individual tray, thereafter, the supply inlet in a commercially available active energy rays radiation unit (manufactured by ICI Co., Ltd. and sold under the trade name of LUXOR) was located for 1-minute visible rays irradiation, whereby the light-curing impression material was cured for precise impression-taking.

COMPARATIVE EXAMPLE 1

Using the conventional dental tray, the denture base of a plate denture (complete denture) for the full upper jaw was prepared by an indirect method in the following manner.

(1) A ready-made tray bearing relative resemblance in size and form to the upper edentulous jaw was selected from a number of ready-made metallic trays having various sizes and forms. Then, an alginate impression material was placed on the inside face of the selected tray, and was pressed against an application surface to set it until a preliminary impression was obtained.

(2) Gypsum slurry was poured into the preliminary impression obtained. After setting of gypsum, a gypsum model was removed from the preliminary impression.

(3) A resin separating agent was applied on the surface of the gypsum model, while a dough-like self curing resin was pressed against it. That resin was allowed to be cured in this state, and the cured resin was removed from the gypsum model to prepare an individual tray (which was of no transparency and did not transmit the active energy rays).

(4) A rubber based impression material was placed on the inside face of the individual tray obtained, and functional impression manipulations such as muscle trimming were carried out. The rubber base impression material was allowed to be set in this state until a functional impression was obtained.

(5) After the boxing of the obtained functional impression was carried out with wax, gypsum slurry was poured thereinto. After setting of gypsum, the removal of the set gypsum gave a working model.

(6) After a resin separating agent was applied on the surface of the obtained working model, a light-curing resin was pressed against it. In this state, the working model with the light-curing resin being retained thereon was put in an active energy rays radiation unit (manufactured by Dentsply Co., Ltd., and sold under the trade name of TRIAD Curing Unit), where it was irradiated with visible rays for 3 minutes to polymerize and cure that resin.

(7) the working model was taken out of the active energy rays radiation unit along with the light-curing resin, which was in turn separated from the working model, thereby preparing the denture base of a plate denture based on the working model.

COMPARATIVE EXAMPLE 2

With a conventional dental tray, precise impression-taking was carried out in the following manner.

(1) A ready-made tray bearing relative resemblance in size and form to the contour of the application surface was selected from a number of ready-made hard plastic trays having various sizes and forms. Then, an alginate impression material was placed on the inside face of the selected tray, and was pressed against an application surface to set it until a preliminary impression was obtained.

(2) Gypsum slurry was poured into the obtained preliminary impression. After setting of gypsum, a gypsum model was removed from the preliminary impression.

(3) A resin separating agent was applied on the surface of the gypsum model, while a dough-like self curing resin was pressed against it. That resin was allowed to be cured in this state, and the cured resin was removed from the gypsum model to prepare an individual tray.

(4) A silicone impression material was placed on the inside face of the individual tray, and was pressed against an application surface. Thereafter, the silicone impression material was permitted to be set until a precise impression was obtained.

Table 1 sets forth the purposes and properties of the dental trays used in Examples 1, 2 and Comparative Example 1, and Table 2 shows the fitting accuracy of the denture base of plate dentures obtained in Examples 1, 2 and Comparative Example 1 and the time periods required for the preparation thereof.

TABLE 1

|  |  | Purposes | Heat Softening Property | Active Energy Rays-Transmitting Property |
|---|---|---|---|---|
| Example 1 |  | Preparation of Denture Base | Softened at 60° C. | Good |
| Example 2 |  | Preparation of Denture Base | Softened at 50° C. | Good |
| Comparative Example 1 | Ready-Made Tray | Preliminary Impression-Taking | No Heat Softening Property | Not Transmitted |
|  | Individual Tray | Precise Impression-Taking | No Heat Softening Property | Not Transmitted |

TABLE 2

|  | Fitting Accuracy of Denture Base | Time Required for Denture Base Preparation |
|---|---|---|
| Example 1 | Good | 30 minutes |
| Example 2 | Good | 30 minutes |
| Comparative Example 1 | No Good | 180 minutes |

In Table 2, the fitting accuracy of the denture bases was measured by placing a silicone base try-in testing material (manufactured by G-C Dental Industrial Corp., and sold under the trade name of Fit Checker) on the side of each denture base facing the mucosal face of the mouth for try-in. Then, the fitting accuracy of each denture base was expressed in terms of the amount of the testing material deposited and remained on the mucosal-side face thereof. That is, very small and considerably large amounts of the deposits were estimated to be "good" and "no good", respectively. The time period required for the preparation of each denture base is shown in the total actual time required for preparing the denture bases of plate dentures according to Examples 1, 2 and Comparative Example 1.

As shown in Tables 1 and 2, the dental tray formed of the material having both the active energy rays-transmitting property and heat softening property according to the present invention makes it easy to form an individual tray, using its heat softening property, and permits a light-curing resin placed on its inside face to be polymerized and cured in situ and simultaneously with functional impression-taking, using its active energy rays-transmitting property. The epoch-making is that, since the tray can easily be separated from the cured resin through the re-use of its heat softening property after curing of the resin, the cured resin directly defines the denture base of a plate denture with no need of preparing any gypsum or working model. As a result, the time period required for the preparation of the denture base of a plate denture is reduced to a very short time of 30 minutes, and much more excellent fitting accuracy is afforded to the denture base of a plate denture.

In the preparation of the plate denture by indirect method wherein the conventional dental tray was used, as shown in Comparative Example 1, however, that tray had neither active energy rays-transmitting property nor heat softening property, and was designed on the conception that it had to be used only for impression-taking. Therefore, it is indispensable to use the step for reproducing the intramouth state on a working model, which is found to offer problems in connection with accuracy errors or reproducibility of details. As a matter of course, the denture base of a plate denture obtained with such a working model that have the problems as mentioned above is unsatisfactory in respect of fitting accuracy. In addition, the time required for the denture base of a plate denture is so extended that the labor and the number of instruments required are increased to a considerable degree.

Table 3 sets forth the purposes and properties of the dental trays used in Example 3 and Comparison Example 2, and Table 4 shows the possibility of a light-curing impression material for use with precise impression-taking and the time required for precise impression-taking.

TABLE 3

| | | Purposes | Heat Softening Property | Active Energy Rays-Transmitting Property |
|---|---|---|---|---|
| Example 3 | | Precise Impression-Taking | Softened at 55° C. | Good Good |
| Comparative Example 2 | Ready-Made Tray | Preliminary Impression-Taking | No Heat Softening Property | Not Transmitted |
| | Individual Tray | Precise Impression-Taking | No Heat Softening Property | Not Transmitted |

TABLE 4

| | Use of Light-Curing Impression Material for Precise Impression | Time Required for Precise Impression-Taking |
|---|---|---|
| Example 3 | Possible | 20 minutes |
| Comparative Example 2 | Impossible | 110 minutes |

As understood from Tables 3 and 4, the dental tray formed of the material having both active energy rays-transmitting property and heat softening property according to the present invention makes it easy to form an individual tray for precise impression-taking, using its heat softening property, and permits a light-curing impression material placed on the inside face of the individual tray to be uniformly polymerized and cured within a short time period, using its active energy rays-transmitting property. Thus, the present dental tray is suitable for precise impression-taking with a light-curing impression material. As a result, the present invention has a very excellent characteristic feature that an individual tray can be prepared directly therefrom for precise impression-taking without any troublesome steps of forming a preliminary impression and a gypsum model, and can considerably shorten the time required for precise impression-taking.

In the precise impression-taking with the conventional dental tray, as exemplified in Comparative Example 2, however, it is required that a preliminary impression be first obtained to form a gypsum model, and a self curing resin be used on the gypsum model to form an individual tray. Thus, the time required for precise impression-taking is very extended, and any light-curing impression material cannot be used for precise impression-taking, since the obtained individual tray has no active energy rays-transmitting property.

APPLICATION EXAMPLE 1

With the partial tray prepared in Example 2, a light-curing composite resin filled in a plurality of teeth cavities was polymerized and cured in the following manner.

(1) A spacer having a thickness of about 1 mm was placed in class 1 cavities formed in the first and second molar teeth of the right lower jaw, and the dental tray previously softened in warm water of about 60° C. was put thereover. While the tray was deformed according to the shapes of the teeth, cold water was applied thereon for cooling and hardening, and the spacer was removed from the dental tray to form an individual tray.

(2) The light-curing composite resin was filled in the cavities, followed by form adjustment. Thereafter, the dental tray was put over the resin, and the supply inlet in an active energy rays radiation unit (manufactured by ICI Co., Ltd. and sold under the trade name of LUXOR) was brought into contact with an arbitrary position on the outside face of said tray for 2-minute visible rays irradiation, whereby the light-curing composite resin in the cavities in the two teeth was simultaneously polymerized and cured, followed by the removal of the individual tray.

The light-curing composite resin filled in the cavities in the two teeth was uniformly polymerized and cured.

In the conventional technique for curing a light-curing composite resin filled in a plurality of cavities, it has been required that the operation of polymerization and curing by active energy rays irradiation be repeated for each cavity. With the present dental tray, however, it is possible to simultaneously cure the light-curing composite resin filled in a plurality of cavities by single irradiation of active energy rays. Thus, the dental tray of the present invention has the advantage that the irradiation of active energy rays conventionally effected for each cavity can be applied simultaneously to a plurality of cavities.

What is claimed is:

1. A dental tray of a shape suitable for direct contact with the mucosal surface of the mouth and capable of retaining an impression making material thereon, comprising:

a thermoplastic resin material transparent to activating light energy radiation and which is softenable at a temperature ranging from 40°-70° C.

2. The dental tray of claim 1, wherein said thermoplastic resin material is polystyrene, a polystyrene derivative, poly(meth)acrylate, a poly(meth)acrylate derivative, polytetrafluoroethylene, a derivative of polytetrafluoroethylene, polyvinylfluoride, a derivative of polyvinylfluoride, polychlorotrifluoroethylene, a derivative of polychlorotrifluoroethylene, polybutadiene, a derivative of polybutadiene, polyisoprene, a derivative of polyisoprene, polyurethane, a derivative of polyurethane or an ethylene copolymers.

3. The dental tray of claim 1, wherein said thermoplastic resin material is an ionomer resin of an ethylene copolymer selected from the group consisting of ethylene/acrylic acid copolymers, ethylene/methacrylic acid copolymers, ethylene/itaconic acid copolymers, ethylene/methyl maleate copolymers, ethylene/maleic acid copolymers, ethylene/acrylic acid/methyl methacrylate copolymers, ethylene/methacrylic acid/ethyl acrylate copolymers, ethylene/itaconic acid/methyl methacrylate copolymers, ethylene/methyl maleate/ethyl acrylate copolymers, ethylene/methacrylic acid/vinyl acetate copolymers, ethylene/acrylic acid/vinyl alcohol copolymers, ethylene/propylene/acrylic acid copolymers, ethylene/styrene/acrylic acid copolymers, ethylene/methacrylic acid/acrylonitrile copolymers, ethylene/fumaric acid/vinyl methyl ether copolymers, ethylene/vinyl chloride/acrylic acid copolymers, ethylene/vinylidene chloride/acrylic acid copolymers, ethylene/vinyl fluoride/methacrylic acid copolymers, ethylene/chlorotrifluoroethylene/methacrylic acid copolymers, wherein the metal ion reacted with said copolymer to form said ionomer resin is a metal selected from the group consisting of $Na^+$, $K^+$, $Li^+$, $Cs^+$, $Ag^+$, $Cu^+$, $Mg^{2+}$, $Ca^{2+}$, $Sr^{2+}$, $Ba^{2+}$, $Cu^{2+}$, $Sn^{2+}$, $Fe^{2+}$, $Ni^{2+}$, $Zn^{2+}$, $Al^{3+}$, $Sc^{3+}$, $Fe^{3+}$, or $Yt^{3+}$.

4. The dental tray of claim 1, wherein the thermoplastic resin material of said tray contains a filler in an amount up to less than 70 wt. % based on the total weight of the dental tray.

5. The dental tray of claim 4, wherein said filler is calcium carbonate, titanium dioxide, zirconium silicate, aluminum silicate, silica, a MMA polymer, a polyvinylchloride powder, alumina, glass, kaolin, anhydrous silicic acid or hydrous silicic acid.

* * * * *